United States Patent [19]
Fowler

[11] 3,933,047
[45] Jan. 20, 1976

[54] METHOD AND MEANS FOR GAS SAMPLING IN MASS SPECTROMETRY
[75] Inventor: Peter Fowler, Ipswich, Mass.
[73] Assignee: Cabot Corporation, Boston, Mass.
[22] Filed: Aug. 15, 1974
[21] Appl. No.: 497,752

[52] U.S. Cl............................. 73/421.5 R; 250/288
[51] Int. Cl.²......................................... G01N 1/22
[58] Field of Search........... 250/288; 73/421.5 R, 42

[56] References Cited
UNITED STATES PATENTS
2,393,650  1/1946  Metcalf.............................. 250/288
2,569,032  9/1951  Washburn........................... 250/288
3,427,858  2/1969  Morrison................................ 73/42

Primary Examiner—S. Clement Swisher
Attorney, Agent, or Firm—Jack Schuman; Barry R. Blaker; Lawrence A. Chaletsky

[57] ABSTRACT

There is disclosed herein a method and means for the collection and introduction of sample gases into a mass spectrometer gas analyzer.

17 Claims, 1 Drawing Figure

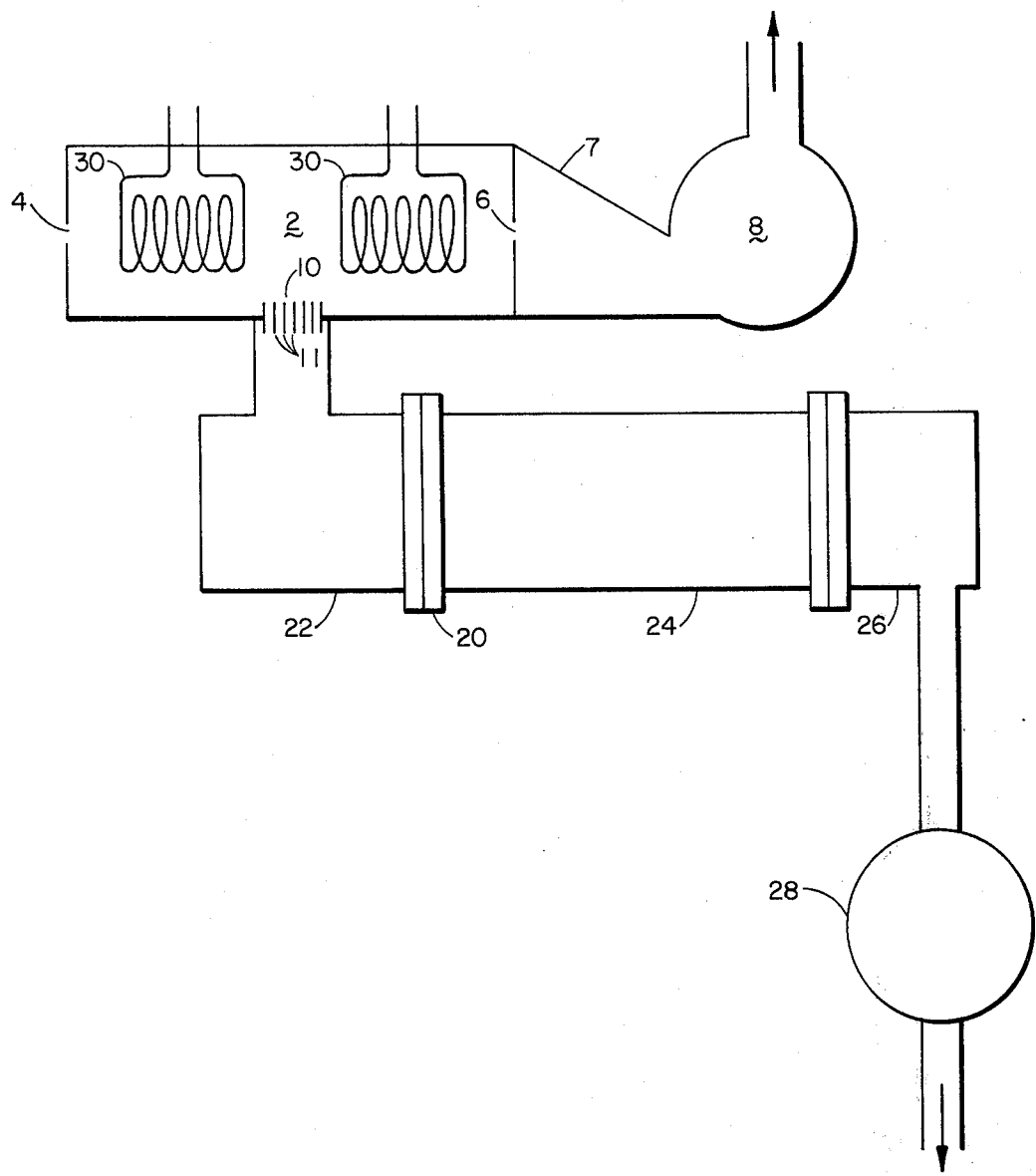

METHOD AND MEANS FOR GAS SAMPLING IN MASS SPECTROMETRY

FIELD OF THE INVENTION

The present invention relates generally to gas analysis by means of mass spectroscopy and is more particularly concerned with an improved method and means for the collection and introduction of gas samples into mass spectrometers.

The quantitative and qualitative analysis of gases by mass spectroscopic techniques is a well-developed and actively pursued art. In mass spectroscopic gas analysis the interior of the mass spectrometer is maintained at a relatively extremely low pressure, for instance, of no more than about $10^{-2}$ Torr. Accordingly, in operations of a generalized mass spectrometer gas analyzer, the sample gas under test is admitted, under vacuum, into the ion source of the mass spectrometer wherein the sample gas is ionized such as by electron bombardment thereof. The resulting ion beam is then projected downstream, usually through a preliminary set of "defocussing" slits, through an analyzer which generally comprises a controllable magnetic field oriented perpendicularly to the axis of the ion beam. The magnetic field thus acts to "focus" or cause each specie of ion or ion fragment forming part of the iron beam to describe a definite characteristic trajectory, the radius of trajectory being dependent upon the mass-to-charge ratio of the particular ion or ion fragment specie being acted upon by the magnetic field. Stationed at the end of the ion beam path is an ion collector which, in association with appropriate electronics, is responsive to the impact thereagainst of those ions and ion fragments not segregated out of the beam by the analyzer. By scanning the analyzer over a range or spectrum of magnetic field strengths, the ion collector is made to quantitatively respond to different ion mass species in the sample gas ion beam.

Variations on the above-outlined theme of mass spectrometer gas analyzer operations are also known. For instance, time of flight mass spectrometers depend upon accelerator components which accelerate the ions and ion fragments formed in the ion source. Here, the ion beam is subjected to controlled acceleration forces generated by a dynamic electric field. For a gas sample containing various charged ion species, each mass-to-charge specie of the sample has associated with it a unique flight time in the dynamic electric field, which time is measured. Accordingly, the various particles are resolved according to their mass-to-charge ratios by recording differences in their flight times in the dynamic electric field. Whatever the precise mode of operations employed in mass spectrometer gas analyzers, however, all are characterized by their operations under relatively extremely low pressure, by their application of an ionizing charge to the sample gas molecules undergoing analysis and by their selective measurement of parameters which are directly relatable to mass-to-charge relationships of the ionized species of the sample gas.

In view of society's intense concerns relating to pollution control, the preservation of health of industrial workers and environmental protection, it has become of paramount importance to provide gas analyzing apparatuses which are capable of resolving and detecting trace quantities of adulterant gases in ambient air volumes. While mass spectroscopy has long been employed in the analysis of trace gases, the application of this technique to ambient air and pollution-related investigations has heretofore been generally limited due to the fact that prior art mass spectroscopy generally requires relatively arduous and time consuming gas sampling techniques and preparation of gas samples for introduction into the relatively high vacuum environment of the mass spectrometer. Thus, despite known benefits of accuracy and sensitivity of mass spectroscopic analysis of gases, the use of mass spectroscopy in analyzing ambient air samples has suffered from the fact that the analytical information outputs of such apparatuses are nor normally available within a sufficiently short time subsequent to sampling of the gas. Generally, there exists a requirement that the analysis be substantially within real time, in other words, within a few seconds of sampling. In view of the present invention, however, these and other problems related to mass spectroscopic analysis of gases have been resolved or at least substantially ameliorated.

OBJECTS OF THE INVENTION

It is a principal object of the invention to provide a novel method for introduction of sample gases into a mass spectrometer gas analyzer.

It is another object of the invention to provide a novel method for sampling of gases at atmospheric pressures and introducing compositionally representative samples thereof into a mass spectrometer gas analyzer.

It is another object of the invention to provide a rapid and accurate method for continuously sampling gases at atmospheric pressures and introducing such samples into a mass spectrometer gas analyzer in such a manner as to obtain rapid response to changes in the composition of the gas being sampled.

It is another object of the invention to provide a rapid method for continuously sampling gases and introducing a continuous accurate gas sample flow into a mass spectrometer gas analyzer, which method is characterized by its freedom from deleterious occlusionary phenomena and its relative temperature insensitivity.

It is another object of the invention to provide a method for continuously sampling gases at atmospheric pressure and introducing samples thereof into a mass spectrometer gas analyzer wherein essentially linear pressure to flow relationships are maintained.

It is another object of the invention to provide a novel gas sample inletting device for mass spectrometer gas analyzers.

It is another object of the invention to provide a novel gas sample inletting device for mass spectrometer gas analyzers which provides for continuous and rapid sampling and introduction of compositionally representative gas samples into the gas analyzer.

It is still another object of the invention to provide a novel gas sample inletting device for mass spectrometer gas analyzers which provides for continuous sampling of gases under atmospheric pressure and introduction thereof into a gas analyzer while maintaining essentially linear pressure to flow relationships and stable analyzer working conditions.

It is yet another object of the invention to provide a novel gas sample inletting device for continuously sampling gases and delivering compositionally representative samples thereof into a mass spectrometer gas analyzer, which device is characterized by rugged construction; freedom from occlusionary phenomena and relative insensitivity to temperature variation.

Other objects and advantages of the invention will in part be obvious and will in part appear hereinafter.

GENERAL DESCRIPTION OF THE INVENTION

The method of the invention generally comprises extracting sample gas from the source environment and flowing it through an enclosed zone of intermediate reduced pressure, the flow of said gas into and out of said zone being under critical flow conditions, while causing a portion of the sample gas in said zone to flow under free molecular flow conditions into an ion source generator of a mass spectrometer gas analyzer.

The apparatus of the invention generally comprises an intermediate vacuum chamber equipped with a sample inlet orifice and a sample outlet orifice and means to place said outlet orifice in operative communication with a fore pump. Said fore pump and sample inlet and outlet orifices are adapted to provide critical flow of the sample gas through each of said inlet and outlet orifices. Additionally, there is provided a separate sampling port adapted for free molecular flow of sample gas from the interior of said vacuum chamber into the ion source of a mass spectrometer gas analyzer.

THE DRAWING

The drawing forming part hereof is a schematic, longitudinal, partly sectional view of the gas sampling device of the invention shown in cooperative arrangement with a mass spectrometer gas analyzer.

DESCRIPTION OF PREFERRED EMBODIMENTS

Referring now to the drawing, the gas sample inletting device of the invention generally comprises vacuum chamber 2 equipped with inlet orifice 4 and outlet orifice 6. Outlet 6 is in operative communication, through tubulation 7, with a vacuum fore pump 8. In operations, it is essential that the sample gas flow through both inlet orifice 4 and outlet orifice 6 under critical flow conditions in order to assure (a) preservation of an essentially linear relationship between sample gas source pressure and the pressure in chamber 2, and (b) extraction of compositionally representative gas samples from the source environment. Failure to preserve said linear relationship and/or said compositionally representative sample in chamber 2 can, of course, lead to faulty and/or more difficult analysis of the gas. For the purposes of the present invention, "critical flow" is defined as that gas flow rate through orifices 4 and 6 which cannot be further increased simply by further decreasing the pressure on the low pressure sides of each of orifices 4 and 6. Critical flow can also be said to involve the achievement of sonic linear velocity of the gas flowing through the throats of the respective inlet and outlet orifices 4 and 6. For operations over a wide range of Reynold's numbers, it is also desirable that the internal diameter of the enclosing apparatus immediately downstream of each orifice, i.e., chamber 2 and tubulation 7, be at least five times that of the diameter of its associated upstream orifice. Further, it will also be apparent that critical flow through orifices 4 and 6 is achievable only when sufficient threshold pressure drops are generated thereacross. Accordingly, it is also important that the vacuum fore pump 8 associated with the inletting device of the invention be of sufficient capacity as to develop these threshold pressure drops. Critical flow of the sample gas through orifices 4 and 6 serves to isolate the intermediate low pressure in the chamber 2 from both the relatively high pressure of the source from which the sample gas is extracted and the pressure downstream of orifice 6, thereby to establish the linear relationship between the gas source and chamber 2 pressures, mentioned above.

The minimum pressure ratio which must be maintained across each of the orifices 4 and 6 for critical flow to occur therethrough is:

$$\frac{p_2}{p_1} = \left[\frac{2}{1+k}\right]^{\left[\frac{k}{k-1}\right]}$$

where $k$ is the ratio of specific heats of the gas; $p_1$ is the pressure, in Torr, of the sample gas upstream from the orifice and $p_2$ is the pressure, in Torr, of the sample gas downstream of the orifice. Thus, in the present invention, each of the inlet and outlet orifices are operated under critical flow conditions and the pressure in chamber 2 between said orifices will be directly proportional to the pressure of the atmosphere being sampled. Where the gas to be sampled is air, the value for $k$ is about 1.405. Thus, where air at, say 100°C, is to be sampled, the flow, $W$, thereof through orifice 4 can be generally approximated by the equation:

$W = 8 \ d^2 p_e$ Torr liters per second where $d$ is the orifice 4 diameter given in centimeters and $P_e$ is the pressure, in Torr, of the sample gas in the environment from which it is extracted, in other words, the pressure upstream of orifice 4. Thus, bearing the above information in mind, it will be possible for the practitioner of the invention to suitably design and dimension the chamber 2, inlet orifice 4, outlet orifice 6, tubulation 7 and fore pump 8 so as to provide the requisite critical flow conditions for any given gas intended to be sampled.

Also, in considering the specific characteristics of these structural elements, it is further well to take into account that, in order to achieve the relatively rapid response times of which the present invention is capable, the volume of chamber 2 is preferably chosen so as to provide a sample gas flow rate therethrough sufficient to achieve substantially complete exchange or purge of resident sample gas within about one second or, even more preferably, within about 0.5 second.

It is the principal function of the chamber 2 to provide a substantially continuous supply of compositionally representative sample gas under conditions suitable for admission of a portion thereof into the mass spectrometer analyzer 20 under free molecular flow conditions. Said chamber 2, by virtue of the relatively lower pressure therein as compared to the sample gas pressure of the environment from which it is extracted, results in a considerable and highly desirable lengthening of the mean free path of the gas molecules forming part of the sample. This condition is conducive for the subsequent introduction of a relatively minute proportion of this relatively low pressure gas sample into the mass spectrometer gas analyzer 20 under free molecular flow conditions. In turn, the necessity for free molecular flow of the sample gas from chamber 2 into the mass spectrometer 20 is essential in order that the partial pressure gas relationships in chamber 2 be maintained equal to partial pressure relationships existing in gas analyzer 20.

Thus, it is additionally essential that the sample gas admission port 10, which establishes communication between chamber 2 and the mass spectrometer gas analyzer 20, be adapted to provide for free molecular sample gas flow therethrough. To this end, therefore, admission port 10 comprises one or more passages 11, each of which bears a characteristic dimension no larger than the mean free path of the sample gas in chamber 2 passing through port 10 into high vacuum analyzer 20. Preferably, the characteristic dimension(s) of each passage 11 will be less than about one-third of the mean free path of the sample gas in chamber 2. By "mean free path" is meant the mean distance traveled between successive collisions of one sample gas mollecule with another. For a more complete discussion of the concept of mean free path and suitable equations for determination thereof, reference is specifically made herein to *The Kinetic Theory of Gases*, Leonard B. Loeb, Third Edition, Dover Publication, Inc., New York, 1961, Chapters III and IV. For information concerning specific mean free paths of various gases, reference is also made to Appendices I and III of the above-identified work. As mentioned before, one beneficial role played by vacuum chamber 2 is to increase the mean free path of the sample gas extracted from the source environment. This, of course, aids markedly in solving the problem of providing free molecular flow of a portion of the sample gas in chamber 2 into analyzer 20, since the effectively lengthened mean free path of the sample gas allows for use of admission port 10 dimensions which are sufficiently large as to be practicably fabricated. Thus, admission port 10 may take the form of one or more pinhole apertures through a thin metallic diaphragm or may be formed of a porous material such as glass or ceramic frit or sintered bronze or stainless steel powders. Each of these above-mentioned general port 10 embodiments is possessed of some combination of attributes and deficiencies. For instance, in the case of the pinhole apertured metallic diaphragms, there is provided an admission port 10 system which is desirably rapidly responsive to composition changes in trace gas concentrations in the sample gas. However, said system also tends to be highly temperature sensitive and, moreover, apertures in metallic diaphragms are generally found to be readily occluded by condensed vapors or very small particulate matter which may be ingested with the gas sample. Contrarily, the porous frits and sintered powder metallurgy wares are normally found to be quite temperature insensitive; but they suffer from generally long response times of from about 1 to several seconds and from susceptibility to occlusion by condensed vapors.

I have discovered that one embodiment of admission port 10, possessed of substantially all of the advantages and none of the disadvantages outlined above, can be had by use, under free molecular flow conditions, of one or, preferably, a plurality of capillary passages 11. Where only one capillary is employed, the mass flow rate of the sample gas into the analyzer 20 will, of course, be quite small and could be found deficient in the provision of sufficient sample gas for precise analysis at high signal-to-noise ratios therein. Where a plurality of capillaries are employed, however, the mass flow rate of sample gas into the mass spectrometer gas analyzer 20 can be quite considerable and rapidly responsive and the multiple capillary arrangement will be substantially less sensitive to deleterious occlusion phenomena. A particularly suitable capillary system for use as the admission port 10 in the present invention is fully disclosed in U.S. Pat. No. 3,645,298, Roberts et al., Feb. 29, 1972, wherein there is disclosed a flow control device comprising a bundle of highly collimated, exquisitely arranged capillary passages, each passage being of a preselected small cross-sectional area and wherein the passages have a preselected aspect ratio of cross-sectional area to length. Taking into account that adsorption of sample gas on the surfaces of a multiple metallic capillary admission port 10 will not normally be significant, the time constant, $\tau$, for sample gas flow therethrough is approximated by the equation:

$$\tau = \frac{l^2}{6D}$$

where $l$ is the capillary length in centimeters and $D$ is the diffusion constant. In turn, the diffusion constant, $D$, is derivable by use of the equation:

$$D = \tfrac{2}{3} rv$$

where $r$ is the capillary radius in centimeters and $v$ is the mean molecular velocity in centimeters per second. Where air is the sample gas to be admitted into the mass spectrometer gas analyzer 20, the preferred multiple capillary admission port 10 arrangement may have a capillary length of 0.12 centimeters and a capillary radius of 0.0006 centimeters. The mean molecular velocity of air is approximately $4 \times 10^4$ centimeters per second. Accordingly, substituting these dimensions and velocity into the time constant equation above yields a time constant, $\tau$, of $1.5 \times 10^{-4}$ second. Said constant is sufficiently small as to ensure substantially instantaneous mass spectrometer response to changes in composition of the sample gas introduced into chamber 2.

The sample gas, flowing under free molecular flow conditions through admission port 10, is conducted into ion source 22 of mass spectrometer 20 wherein it is ionized and the resulting ions and ion fragments projected downstream through analyzer section 24 to collector section 26. Vacuum pump 28 serves to establish the working pressure within mass spectrometer 20, which working pressure will, of course, be less than that of chamber 2, for instance as low as $10^{-2}$ Torr and often as low as $10^{-4}$ Torr or even lower. The specific design of the mass spectrometer gas analyzer 20 is not normally critical in the practice of the present invention. Accordingly, gas analyzer details pertaining to ionization of the sample gases, treatment of the ionized sample gas in order to separate the ions and ion fragments by means of mass-to-charge phenomenon and ion collection, measurement and data processing do not form essential elements of the invention. Suffice it to say, therefore, that mass spectrometer gas analyzers generally suitable for use in the present invention are disclosed in such patent literature as: U.S. Pat. No. 3,582,648, Anderson, June 1, 1971; U.S. Pat. No. 3,586,853, Vestal, June 22, 1971; U.S. Pat. No. 3,596,088, Cohen et al., July 27, 1971; U.S. Pat. No. 3,596,091, Helmer et al., July 27, 1971; U.S. Pat. No. 3,601,607, Wasserburg et al., Aug. 24, 1971; U.S. Pat. No. 3,610,291, Major, Jr., Oct. 5, 1971; U.S. Pat. No. 3,610,922, Werner, Oct. 5, 1971; U.S. Pat. No. 3,617,736, Barnett et al., Nov. 2, 1971; U.S. Pat. No. 3,621,242, Ferguson et al., Nov. 16, 1971; U.S. Pat. No. 3,641,339, McCormich, Feb. 8, 1972; U.S. Pat. No. 3,641,340, Van Der Grinten et al., Feb. 8, 1972; U.S. Pat. No. 3,648,046, Denison et al., Mar. 7, 1972; U.S. Pat. No. 3,654,457, Yano et al., Apr. 4, 1972.

A working example of the sample gas inletting system of the invention, adapted specifically for sampling of ambient air under a pressure of approximately 760 Torr, is as follows:

Material of construction — stainless steel
Inlet orifice 4 diameter — 0.025 centimeter
Chamber 2 diameter — 1.7 centimeters
Chamber 2 length — 9.5 centimeters
Outlet orifice 6 diameter — 0.336 centimeter
Tubulation 7 diameter — 1.68 centimeters
Fore pump 8 capacity — 2.66 liters/second
Resident time in chamber 2 — 0.1 second
Working pressure chamber 2 — 4.2 Torr
Admission port 10 — comprises a stainless steel bundle of 2500 parallel capillaries 11, each of 0.00065 centimeter diameter and 0.065 centimeter length
Vacuum pump 28 — diffusion type — capacity — 10 liters/second at ion source 22
Ion source working pressure — $2 \times 10^{-5}$ Torr In another preferred embodiment of the invention, heating means 30 are provided for maintaining the sample gas in chamber 2 at above the dewpoint thereof. This last-mentioned feature, of course, mitigates against condensation of the sample gas components as they flow through admission port 10, thereby aiding in the prevention of blockage of said port 10 as well as further insuring that the composition of the sample gas flowing into the mass spectrometer gas analyzer 20 will be compositionally representative of the sample gas of the environment from which it is originally extracted. Of course, the admission port 10 may itself be equipped with heating means (not shown) adapted to carry out a similar function.

Obviously, many changes and modifications may be made in the operations and design of the gas sample inletting system explicitly described above without departing from the intended scope and spirit of the invention. For instance, the sample gas may be treated in a number of ways prior to admission into the chamber 2, such as by chromatographic or other separations of one or more components thereof in order to prevent interferences during mass spectrographic analyses thereof. Also, if condensible components of the sample gas are not desired to be determined by mass spectrographic analysis, it is also within the purview of the invention to pre-treat the environmental gas sample by condensation prior to entry into chamber 2.

It should, therefore, be noted that the several specific embodiments of the invention specifically described hereinbefore are to be considered in all respects as illustrative and not limiting, and all changes coming within the meaning and equivalency range of the appended claims are intended to be embraced therein.

What is claimed is:
1. A method for sampling gas from an environment of comparatively high pressure and introducing same into a mass spectrometer gas analyzer under relatively low pressure which comprises: providing an enclosed zone having an inlet in communication with said environment, an outlet and a separate sample admission port in communication with said mass spectrometer; maintaining the pressure in said enclosed zone intermediate that of said environment and that of said mass spectrometer; causing sample gas from said environment to flow through said inlet and said outlet under critical flow conditions; and causing a portion of sample gas contained in said enclosed zone to flow through said sample admission port under free molecular flow conditions and into said mass spectrometer gas analyzer.

2. The method of claim 1 wherein said inlet and said enclosed zone are each of essentially circular cross-sectional geometry and wherein the diameter of said enclosed zone is at least five times the diameter of said inlet.

3. The method of claim 1 wherein said sample gas is flowed through said enclosed zone at a rate sufficient to effectuate a substantially complete exchange thereof within one second.

4. The method of claim 1 wherein said sample gas is flowed through said enclosed zone at a rate sufficient to effectuate a substantially complete exchange thereof within 0.5 second.

5. The method of claim 1 wherein the pressure in said enclosed zone is maintained sufficiently below that of the environmental pressure as to substantially lengthen the mean free path of the sample gas introduced thereinto.

6. The method of claim 1 wherein said sample admission port comprises a plurality of capillary passages each having a diameter smaller than the mean free path of the sample gas contained in said enclosed zone.

7. The method of claim 1 wherein said sample gas is air, said environment has a pressure of about 760 Torr and said mass spectrometer gas analyzer is operated at a maximum pressure of about $10^{-2}$ Torr.

8. The method of claim 7 wherein said enclosed zone is maintained at a pressure of about 4.2 Torr.

9. A gas sampling and inletting device for mass spectrometer gas analyzers which comprises a vacuum chamber having separate sample gas inlet, outlet and analyzer admission port means; said inlet means and outlet means each being adapted to foster critical flow of sample gas therethrough; said outlet means being adapted for communication with vacuum pumping means; said analyzer admission port means being stationed intermediate said inlet and outlet means, being adapted for communication with the ion source of a mass spectrometer gas analyzer and being adapted to foster free molecular flow therethrough of sample gas from said vacuum chamber.

10. The gas sampling and inletting device of claim 9 in combination with vacuum fore pump means in communication with said outlet means, said vacuum fore pump means being of sufficient capacity to reduce the pressure in said vacuum chamber and to establish critical flow of sample gas through said inlet and outlet means.

11. The gas sampling and inletting device of claim 9 wherein each of said inlet means, outlet means, said vacuum chamber and means for establishing communication between said outlet means and vacuum pumping means are essentially circular in cross-sectional geometry and wherein the diameter of said vacuum chamber is at least five times the diameter of said inlet means and wherein the diameter of said means for establishing communication is at least five times the diameter of said outlet means.

12. The gas sampling and inletting device of claim 9 wherein said analyzer admission port means comprises a thin metallic diaphragm having one or more pinhole apertures therethrough.

13. The gas sampling and inletting device of claim 9 wherein said analyzer admission port means comprises a porous ceramic or sintered metallic powder ware.

14. The gas sampling and inletting device of claim 9 wherein said analyzer admission port means comprises at least one capillary.

15. The gas sampling and inletting device of claim 14 wherein said analyzer admission port means comprises a plurality of highly collimated, parallel capillaries.

16. The gas sampling and inletting device of claim 9 wherein said inlet means consists of one or more orifices.

17. The gas sampling and inletting device of claim 9 wherein said outlet means consists of one or more orifices.

* * * * *